(12) United States Patent
Jiang et al.

(10) Patent No.: US 12,016,663 B2
(45) Date of Patent: Jun. 25, 2024

(54) PULSE DIAGNOSIS APPARATUS (71) Applicant: AU Optronics Corporation, Hsin-Chu (TW)

(72) Inventors: Min-Qian Jiang, Hsin-Chu (TW); Chung-Chin Huang, Hsin-Chu (TW); Yi-Han Chang, Hsin-Chu (TW); Hao-Lun Hsieh, Hsin-Chu (TW)

(73) Assignee: AU OPTRONICS CORPORATION, Hsin-Chu (TW)

( * ) Notice: Subject to any disclaimer, the term of this patent is extended or adjusted under 35 U.S.C. 154(b) by 340 days.

(21) Appl. No.: 17/510,893

(22) Filed: Oct. 26, 2021

(65) Prior Publication Data

US 2023/0028454 A1 Jan. 26, 2023

(30) Foreign Application Priority Data

Jul. 20, 2021 (TW) .................. 110126530

(51) Int. Cl.
*A61B 5/021* (2006.01)
*A61B 5/00* (2006.01)

(52) U.S. Cl.
CPC ........... *A61B 5/021* (2013.01); *A61B 5/6824* (2013.01); *A61B 5/742* (2013.01); *A61B 5/70* (2013.01); *A61B 2562/0247* (2013.01)

(58) Field of Classification Search
CPC ... A61B 5/4854; A61B 5/6824; A61B 5/6835; A61B 5/02116; A61B 5/021; A61B 5/7242; A61B 17/00; A61B 2017/00367; A61B 2017/347; A61B 5/02438; A61B 6/04; A61B 2090/0811; A61B 2090/0812; A61B 2017/2946; A61B 2562/0247;
(Continued)

(56) References Cited

U.S. PATENT DOCUMENTS 6,432,060 B1 * 8/2002 Amano ................. A61B 5/021
  600/490
2005/0038347 A1 * 2/2005 Suzuki ............... A61B 5/02444
  600/500
(Continued)

FOREIGN PATENT DOCUMENTS

CN    1565378 A  *  1/2005
CN    105030214 A    11/2015
(Continued)

*Primary Examiner* — Daniel L Cerioni
*Assistant Examiner* — Jonathan E. Cooper
(74) *Attorney, Agent, or Firm* — WPAT, P.C (57) ABSTRACT

A pulse diagnosis apparatus includes a base, a bearing and a plurality of sensing module. The base has a motion module. The motion module is disposed on the base and moves back and forward in a first direction. The bearing is disposed on the motion module and includes a first face and a second face. Each sensing module includes a driving element, a flexible element and a sensing unit. The driving element moves in the first direction and passes through the bearing. The driving element includes a first terminal and a second terminal. The first terminal is adjacent to the second face. The second terminal is adjacent to the first face. The flexible element is hitched up the driving element. Two terminals of the flexible element are against the second terminal and the bearing. The sensing unit is disposed on the second terminal.

7 Claims, 10 Drawing Sheets

(58) Field of Classification Search
CPC ............ A61B 5/70; A61B 2017/00398; A61B 2017/00017; A61B 2034/2051; A61B 2017/00402; A61B 1/00042; A61B 17/122; A61B 2034/742; A61B 5/6812; A61B 5/742

See application file for complete search history.

(56) References Cited

U.S. PATENT DOCUMENTS

| | | | | |
|---|---|---|---|---|
| 2008/0103398 A1* | 5/2008 | Huang | ................. | A61B 5/4854 |
| | | | | 600/500 |
| 2010/0022895 A1* | 1/2010 | Kim | ....................... | A61B 5/024 |
| | | | | 600/500 |
| 2014/0323886 A1* | 10/2014 | Lee | ..................... | A61B 5/0255 |
| | | | | 600/500 |
| 2015/0190065 A1* | 7/2015 | Kim | ................... | A61B 5/02427 |
| | | | | 600/479 |
| 2020/0046296 A1* | 2/2020 | Romano | ................ | A61B 5/704 |
| 2022/0361757 A1* | 11/2022 | Al Waked | ............ | A61B 5/0088 |

FOREIGN PATENT DOCUMENTS

| | | | | |
|---|---|---|---|---|
| CN | 105249941 A | | 1/2016 | |
| CN | 106073730 A | | 11/2016 | |
| CN | 106913319 A | | 7/2017 | |
| CN | 108968930 A | * | 12/2018 | ............... A61B 5/02 |
| CN | 109549630 A | | 4/2019 | |
| CN | 211131032 U | | 7/2020 | |
| CN | 108078553 B | * | 2/2021 | ............... A61B 5/02 |
| CN | 112842290 A | | 5/2021 | |

* cited by examiner

PULSE DIAGNOSIS APPARATUS

This application claims priority to Taiwan Application Serial Number 110126530, filed Jul. 20, 2021, which is herein incorporated by reference in its entirety.

BACKGROUND

Field of Invention

The present disclosure relates to a medical device. In particular, the present disclosure relates to a pulse diagnosis apparatus for sensing a pulse of a user by using a configuration of a driving element, a flexible element, and a sensing unit.

Description of Related Art

As Wang Shuhe states in Scripture on Pulses, "it is easy to understand by heart, but difficult to know by finger." The practice of pulse diagnosis in traditional Chinese medicine has always lacked clear quantitative and qualitative standards due to the subjective and empirical nature of passing down finger sensing techniques. Thus, it is difficult to apply pulse diagnosis of Chinese medicine in modern medicine, and difficult to conduct research. Even people studying Chinese medicine finds this troubling, and sees it as a daunting task. Therefore, industry and academic institutions actively research scientific pulse diagnosis apparatuses, treating studies for the objectivity and standardization in Chinese medicine as an important task.

In summary of the above, a designer of the present disclosure studies and designs a type of pulse diagnosis apparatus, for improving faults in convention techniques, thus improving practical application thereof in the industry.

SUMMARY

In light of the above object, the present disclosure provides a pulse diagnosis apparatus, which solves a problem of conventional techniques by adjusting a height of a sensing unit to correspond to pulse diagnosis positions cun, guan, and chi of a wrist of a patient, such that an accuracy of pulse measurement signals is increased.

In light of the above object, the present disclosure provides a pulse diagnosis apparatus, including a base, a bearing, and a plurality of sensing modules. The base has a motion module arranged on the base and movable back and forth along a first direction. The bearing is arranged on the motion module, and a first face and a second face facing each other along the first direction. Each of the sensing modules includes a driving element, a flexible element, and a sensing unit. The driving element passes through the bearing and is movable along the first direction, and includes a first terminal and a second terminal. The first terminal is proximal to the second face, and the second terminal is proximal to the first face. The flexible element sleeves the driving element, and two terminals of the flexible element respectively abut the second terminal and the bearing. The sensing unit is arranged on a terminal face of the second terminal.

In some embodiments of the present disclosure, the present disclosure further includes a plurality of positioning elements, arranged on an inner side of the bearing.

In some embodiments of the present disclosure, one of the positioning elements is proximal to one of the sensing modules.

In some embodiments of the present disclosure, the present disclosure further includes a first assist element arranged at a side of the bearing for fixing each of the driving elements to a position along the first direction.

In some embodiments of the present disclosure, the first assist element includes a button a plurality of electromagnets. The button is arranged on a side of the bearing and is electrically connected to the plurality of electromagnets. The plurality of electromagnets is arranged on the second face and surrounds the first terminals of the plurality of driving elements. When the button is pressed, the plurality of electromagnets conducts electricity and creates a magnetic field, and the electromagnets are attracted in pairs according to the electromagnetic field, such that each of the driving elements is fixed to a position along the first direction.

In some embodiments of the present disclosure, the first assist element includes an operation lever and a lock element. The operation lever is arranged on a side of the bearing, and is connected to the lock element. The lock element corresponds to the plurality of driving elements and is arranged in the bearing. The operation lever allows the lock element to fix each of the driving elements to a position along the first direction.

In some embodiments of the present disclosure, the present disclosure further includes a second assist element arranged on a side of the bearing, for fixing the bearing to a position along a second direction. The second direction is perpendicular to the first direction.

In some embodiments of the present disclosure, the motion module includes a track. The bearing is arranged on the track, and is movable in the second track on the track.

In some embodiments of the present disclosure, the present disclosure further includes an electronic device. Each of the sensing units senses a portion to be sensed and emits a sensing signal. The electronic device is electrically connected to each of the sensing units, and integrates sensing signals as pulse pressure, and displays the pulse pressure.

In summary of the above, the pulse diagnosis apparatus of the present disclosure accurately measures a pulse of a patient by using a configuration of the driving element and the flexible element, to adjust a position of the sensing unit to match pulse diagnosis positions cun, guan, and chi of a wrist of a patient.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

Advantages, features, and technical methods of the present disclosure are described in detail by referencing exemplary embodiments and attached figures for ease of understanding, and the present disclosure can be implemented in different forms, and thus embodiments described herein should not be interpreted to limit the present disclosure. Instead, for a person skilled in the art, the provided embodiments convey a scope of the present disclosure in a more clear, comprehensive, and complete manner, and the present disclosure is only defined by the attached claims.

It should be understood that, even though "first" and "second" can be used in the present disclosure to describe different elements, parts, regions, layers, and/or portions, these elements, parts, regions, layers, and/or portions are not limited by these languages. These language merely distinguish an element, part, region, layer, and/or portion from another element, part, region, layer, and/or portion. Therefore, "first element," "first part," "first region," "first layer," and/or "first portion" described below can also be named "second element," "second part," "second region," "second layer," and/or "second portion," without departing from the spirit and teaching of the present disclosure.

Additionally, words "include" and/or "comprise" indicate an existence of said feature, region, body, step, operation, element, and/or part, and do not exclude the existence or potential addition of one or multiple other features, regions, bodies, steps, operations, elements, parts, and/or combinations thereof.

Unless otherwise defined, languages used in the present disclosure (including technical and academic language) have a same meaning as understood by a person skilled in the art of the field of the present disclosure. It should further be understood that, technical terms such as those defined in conventional dictionaries should be interpreted as having a meaning consistent to related techniques and context of the present disclosure, and not be interpreted as an ideal or overly formal meaning, unless specifically defined herein.

Figure 1:
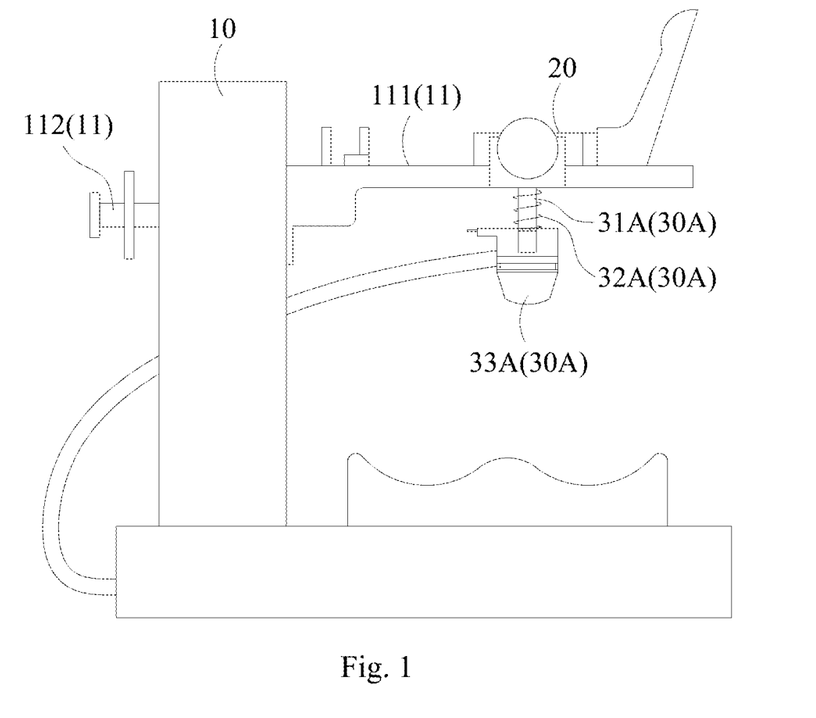
FIG. 1 is a configuration diagram of a pulse diagnosis apparatus according to the present disclosure.
Figure 2:
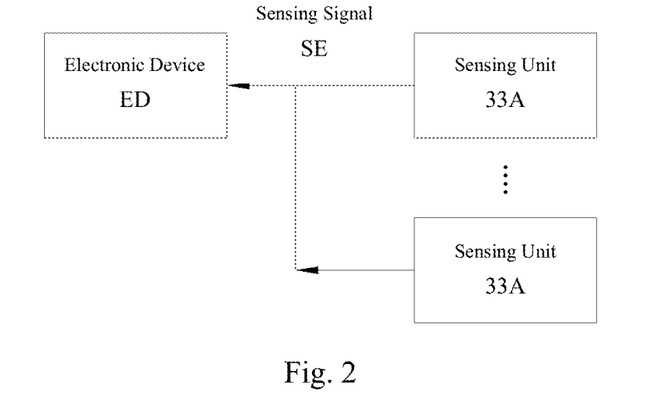
FIG. 2 is a block diagram of a sensing unit and an electronic element according to the present disclosure.
Figure 3A:
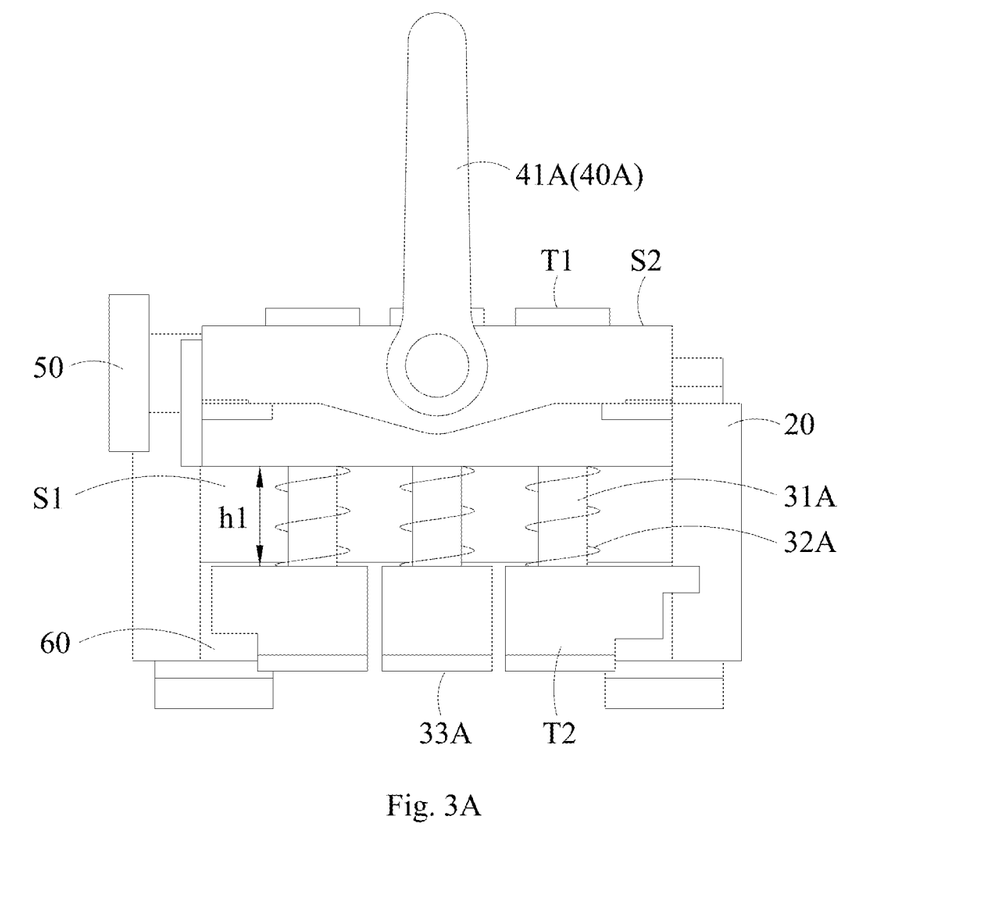
FIG. 3A is a configuration diagram of a sensing module and a first assist element of a first embodiment according to the present disclosure.

FIG. 1 to FIG. 3A are a configuration diagram of a pulse diagnosis apparatus according to the present disclosure, a block diagram of a sensing unit and an electronic element according to the present disclosure, and a configuration diagram of a sensing module and a first assist element of a first embodiment according to the present disclosure. As shown in FIG. 1 and FIG. 3A, a pulse diagnosis apparatus of the present disclosure includes a base 10, a bearing 20, and a plurality of sensing modules 30a. The base 10 has a motion module 11. The motion module 11 is arranged on the base 10 and is movable back and forth along a first direction D1. The bearing 20 is arranged on the motion module 11, and the bearing 20 includes a first face S1 and a second face S2 opposite to each other along the first direction D1. Each of the sensing modules 30A includes a driving element 31A, a flexible element 32A, and a sensing unit 33A. The driving element 31A passes through the bearing 20 and is movable in the first direction D1. The driving element 31A includes a first terminal T1 and a second terminal T2. The first terminal T1 is proximal to the second face S2. The second terminal T2 is proximal to the first face S1. The flexible element 32A sleeves the driving element 31A, and two terminals of the flexible element 32A respectively abut the second terminal T2 and the bearing 20. The sensing unit 33A is arranged on a terminal face of the second terminal T2.

The motion module 11 includes a track 111 and a fastening element 112. The track 111 can be on the base 10 and move along the first direction D1. The fastening element 112 fixes the track 111 to a position in the first direction D1. The bearing 20 is arranged on the track 111 and is movable on the track 111 along a second direction D2 (parallel to the first direction D1), such that a position of the sensing unit 33A approaches a wrist of a patient. For example, the sensing units 33A can be pressure sensors and have similar dimensions, so as to reduce production cost. The amount of sensing unit 33A can be 3, to correspond to pulse diagnosis positions cun, guan, and chi. The total length of the sensing units 33A conforms to the width of three fingers as used in Chinese medicine. The driving element 31A is a screw and is fixed to the bearing 20 by a screw head. The flexible element 32A is a spring. Obviously, the sensing unit 33A, the flexible element 32A, and the driving element 31A can be other elements having similar functions, and are not limited to examples given in the present disclosure.

Figure 4:
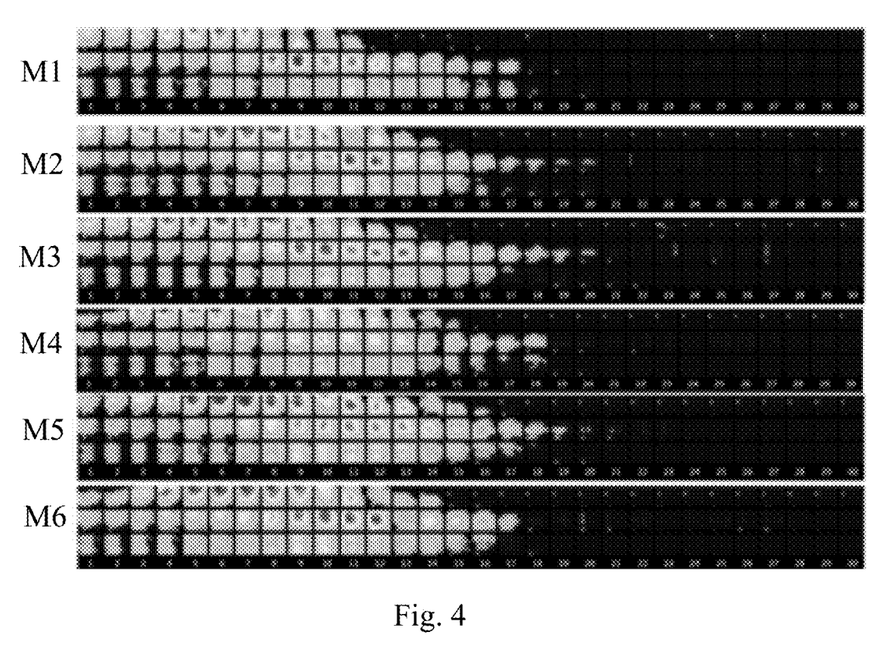
FIG. 4 is a pulse diagram displayed by an electronic element according to the present disclosure.

In the present embodiment, as shown in FIG. 2, a pulse diagnosis apparatus of the present disclosure further includes and electronic device ED. The electronic device ED is electrically connected to each of the sensing units 33A. Each of the sensing units 33A senses a portion to-be-sensed (such as a wrist) and emits a sensing signal SE. Each of the sensing units 33A transmits the sensing measured sensing signal SE to the electronic device ED. The electronic device ED integrates each of the sensing signals SE as pulse pressures and displays pulse pressures as shown in FIG. 4. The electronic device ED can be a computer or a laptop, and can also be other electronic devices capable of data processing, and is not limited to examples given in the present disclosure.

Referring to FIG. 3A, in the present embodiment, a pulse diagnosis apparatus of the present disclosure further includes a first assist element 40A, a second assist element 50, and a plurality of positioning elements 60. The first assist element 40A is arranged on a side of the bearing 20 to fix each of the driving elements 31A to a position in the first direction D1. The second assist element 50 is arranged on a side of the bearing 20 to fix the bearing 20 to a position in the second direction D2. A position of the first assist element 40A is different from a position of the second assist element 50. The side at the position of the first assist element 40A is different from the side at the position of the second assist element 50. The plurality of positioning elements 60 are arranged at an inner side of the bearing 20, and is proximal to the sensing module 30A. The plurality of positioning elements 60 can be visible laser modules (emitting light having wavelength of infrared light). The plurality of positioning elements 60, matching the bearing 20, are movable in the second direction D2 along the track 111 (as shown in FIG. 1), so as to position with respect to pulse diagnosis positions cun, guan, and chi of a wrist. In other words, the plurality of positioning elements 60 assist each of the sensing units 33A to be positioned to pulse diagnosis positions cun, guan, and chi of the wrist, increasing sensing accuracy of each of the sensing units 33A.

In the present embodiment, the first assist element 40A includes an operation lever 41A and a lock element. The operation lever 41A is arranged at an exterior side of the bearing 20 and is connected to the lock element. The operation lever 41A can be an adjustable handle. The lock element corresponds to the plurality of driving elements 31A and is arranged in the bearing 20. The operation lever 41A drives the lock element to fix each of the driving elements 31A to a positon in the first direction D1. For example, turning the operation lever 41A in a clock-wise direction fixes each of the driving elements 31A to the position in the first direction D1, and turning the operation lever 41A in an anti-clock-wise direction releases each of the driving elements 31A.

To be noted, as shown in FIG. 3A, at this moment each of the sensing units 33A does not contact a wrist of a patient. First heights h1 separate each of the sensing units 33A and the bearing 20, and values of the first heights h1 are the same.

Figure 3B:
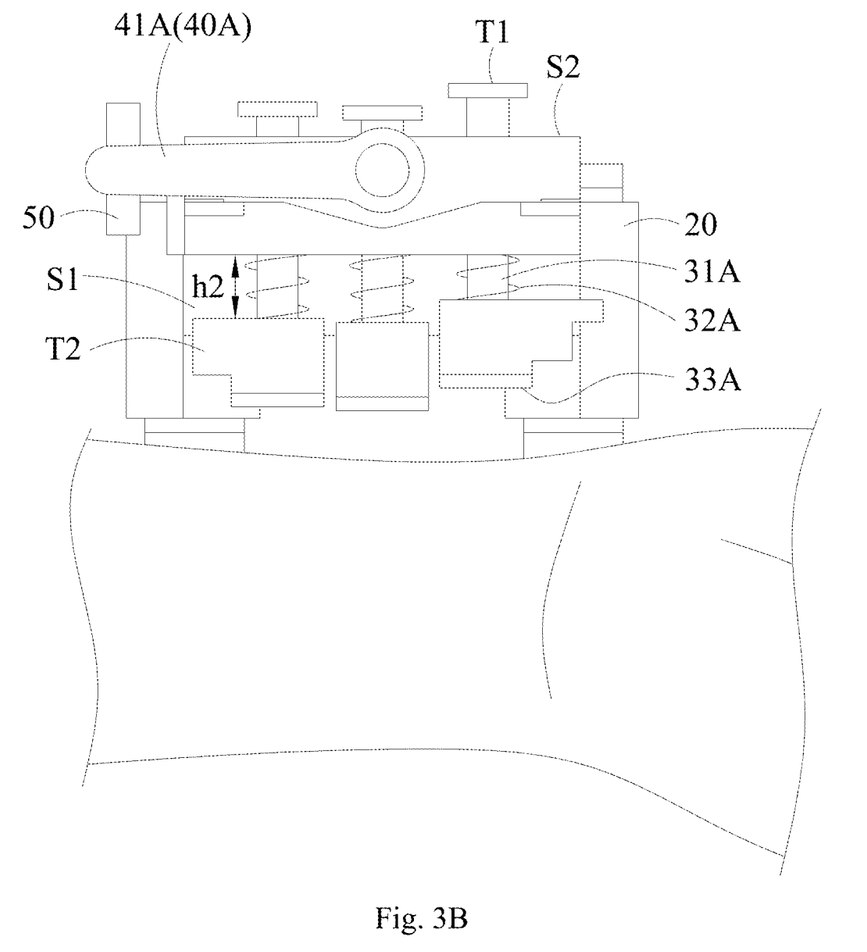
FIG. 3B is a schematic diagram of a sensing module and a first assist element in a first condition of a first embodiment according to the present disclosure.
Figure 3C:
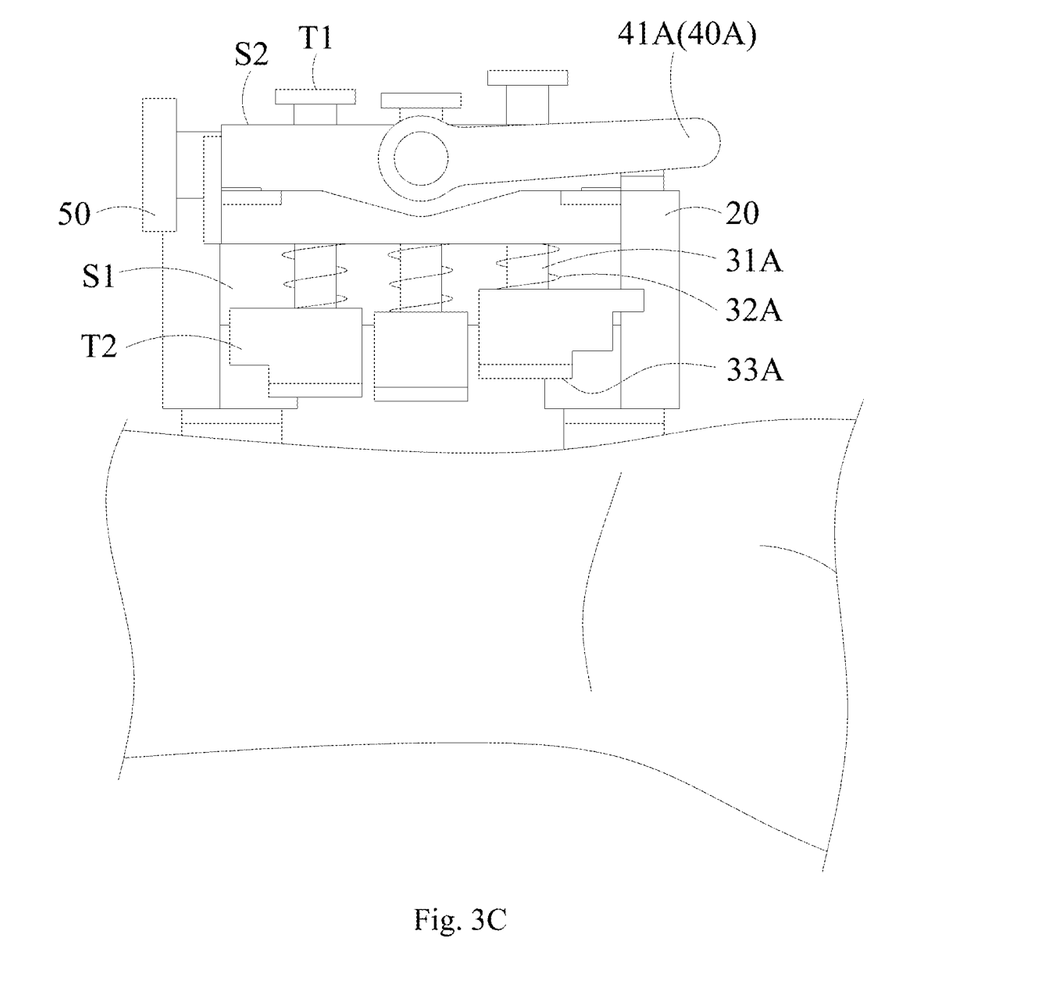
FIG. 3C is a schematic diagram of a sensing module and a first assist element in a second condition of a first embodiment according to the present disclosure.

FIG. 3B and FIG. 3C are a schematic diagram of a sensing module and a first assist element in a first condition of a first embodiment according to the present disclosure, and a schematic diagram of a sensing module and a first assist element in a second condition of a first embodiment according to the present disclosure. As shown in FIG. 3B, the bearing 20 moves on the track 111 to be above a wrist of a patient (as shown in FIG. 1). The second assist element 50 fixes the bearing 20 to a position in the second direction D2. Each of the sensing units 33A contacts the pulse diagnosis positions cun, guan, and chi of the wrist of the patient. A distance separating each of the sensing units 33A and the bearing 20 changes from the first heights h1 (as shown in FIG. 3A) to second heights h2. According to different cun, guan, and chi of a wrist, the second heights h2 can thereby be different. As shown in FIG. 3C, turning the operation lever 41A in a clock-wise direction drives the lock element to fix each of the driving element 31A to a position in the first direction D1, such that each of the driving elements 31A stops moving, increasing the sensing accuracy of each of the sensing units 33A. At this moment, each of the sensing units 33A measures and transmits sensing signals SE (as shown in FIG. 2) to the electronic device 40. The electronic device 40 accordingly displays the pulse of the patient. When the measurement of each of the sensing units 33A ends, the operation lever 41A is turned anti-clock-wise, thereby releasing the fixing of the lock element on each of the driving elements 31A.

FIG. 4 is a pulse diagram displayed by an electronic element according to the present disclosure. As shown in FIG. 4, the electronic device 40 displays corresponding pulses produced by each of the sensing elements 33A in six measurement time periods M1 to M6. Corresponding pulses of each of the measurements M1 to M6 are similar, showing consistency and repeatability of the present disclosure.

Figure 5:
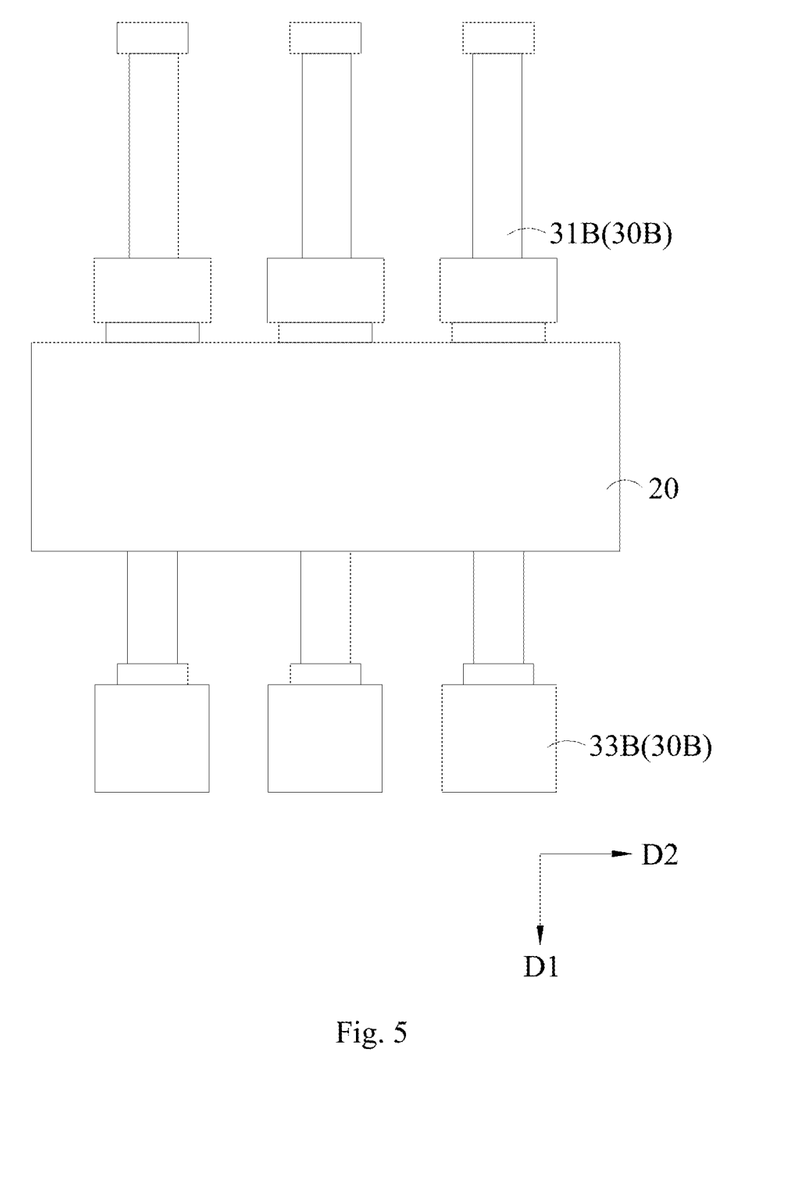
FIG. 5 is a configuration diagram of a sensing module of a second embodiment according to the present disclosure.

FIG. 5 is a configuration diagram of a sensing module of a second embodiment according to the present disclosure. As shown in FIG. 5, each of the sensing modules 30B includes a driving element 31B and a sensing unit 33B. Configuration of the sensing unit 33B is similar to that of the first embodiment, and is similarities are not further described herein. A difference between the second embodiment and the first embodiment of the present disclosure lies in: the driving element 31B is a pneumatic cylinder, and configuration of the flexible element 32A (such as the ones show in FIG. 3A) is not required, such that a movement of the sensing unit 33B in the first direction is smoother. In another embodiment, the driving element 31B is a hydraulic cylinder.

Figure 6A:
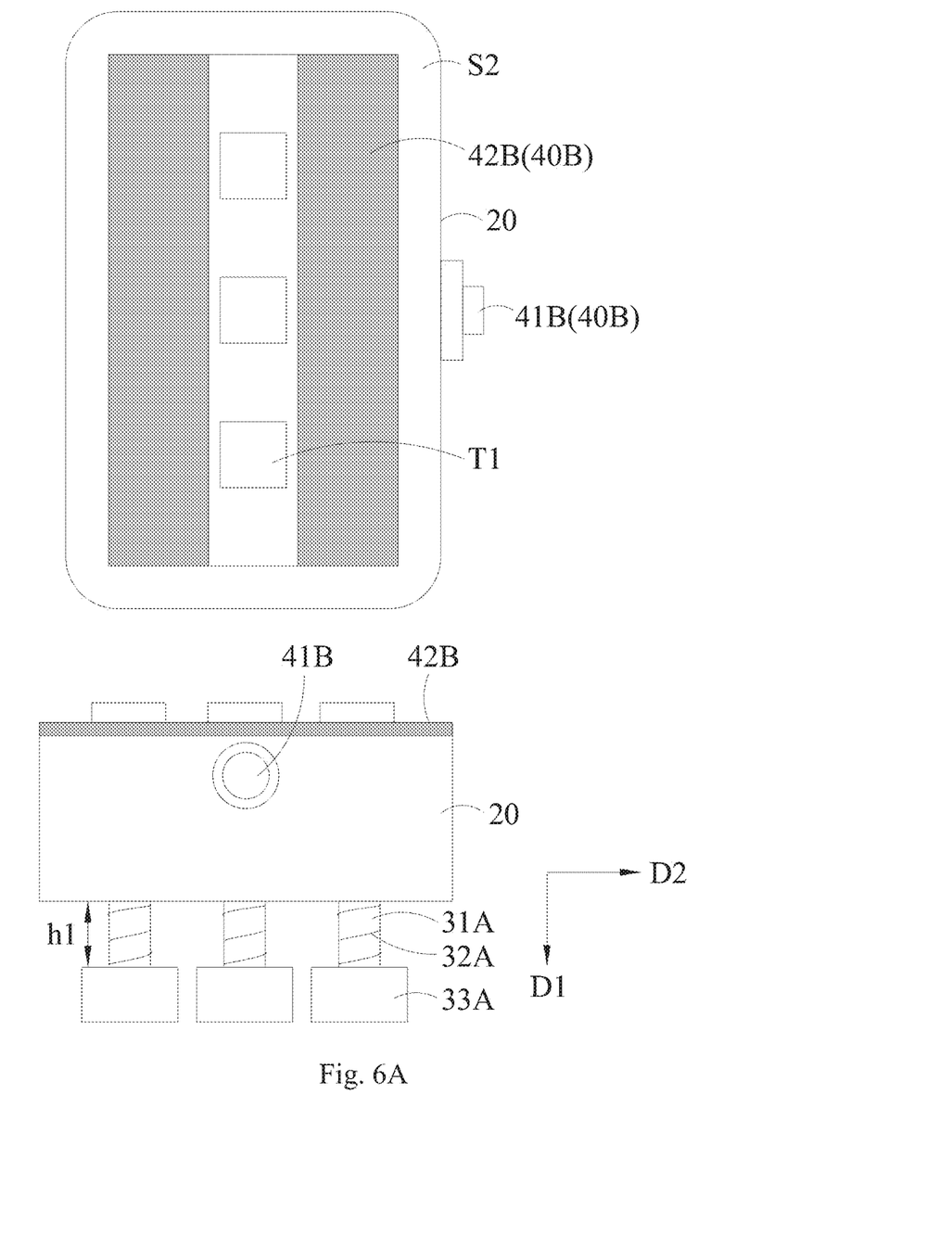
FIG. 6A is a configuration diagram of a first assist element of a second embodiment according to the present disclosure.

FIG. 6A is a configuration diagram of a first assist element of a second embodiment according to the present disclosure. As shown in FIG. 6A, the first assist element 40B includes a button 41B and a plurality of electromagnets 42B. The button 41B is arranged at a side of the bearing 20 and is electrically connected to the plurality of electromagnets 42B. The plurality of electromagnets 42B are arranged at the second face S2 and surround the first terminals T1 of the plurality of driving elements 31A. Triggering the button 41B causes the plurality of electromagnets 42B to conduct electricity and thereby create a magnetic field. The plurality of electromagnets 42B are attracted in pairs according to the magnetic field, so as to fix each of the driving elements 31 to a position in the first direction D1. Similarly, when the plurality of electromagnets 42B are not conducting electricity, each of the sensing units 33A does not contact a wrist of a patient at this moment, each of the sensing units 33A is separated from the bearing 20 by the first heights h1, and values of the first heights h1 are the same.

Figure 6B:
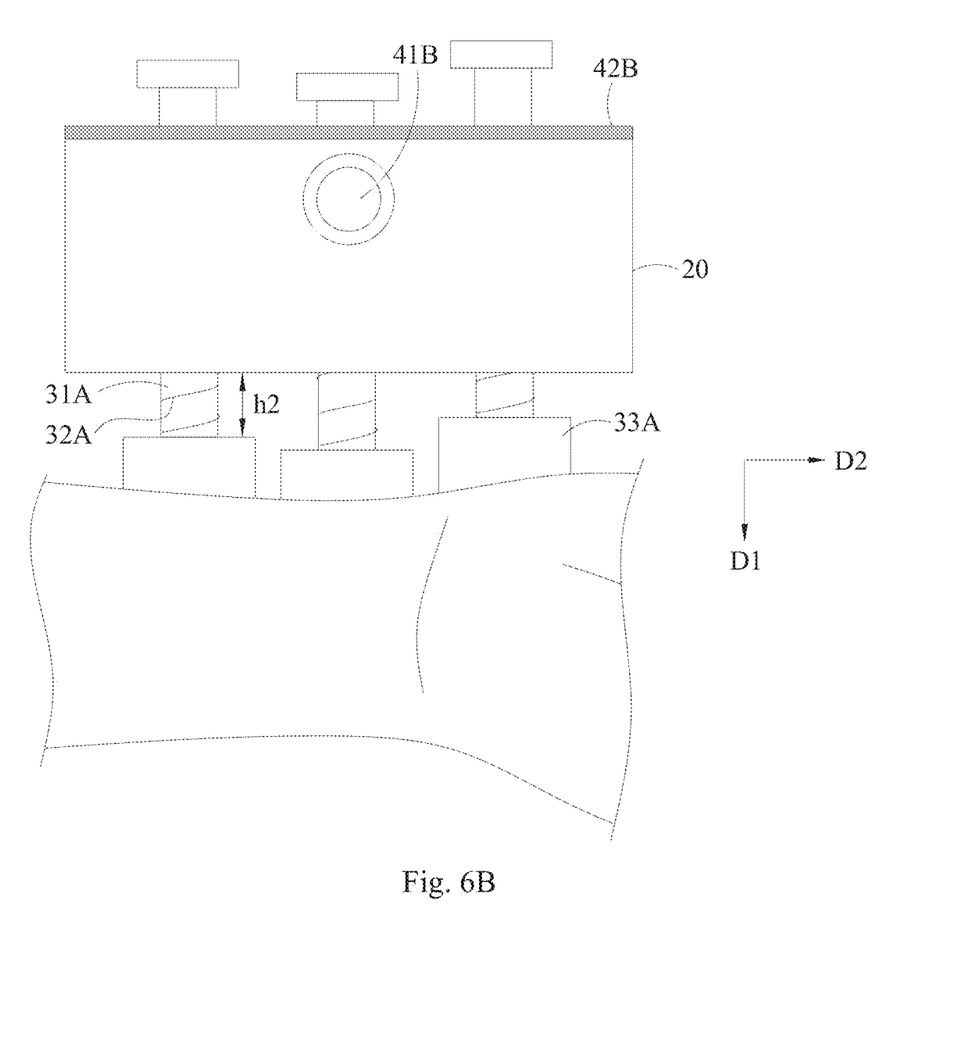
FIG. 6B is a schematic diagram of a sensing module and a first assist element in a first condition of a second embodiment according to the present disclosure.
Figure 6C:
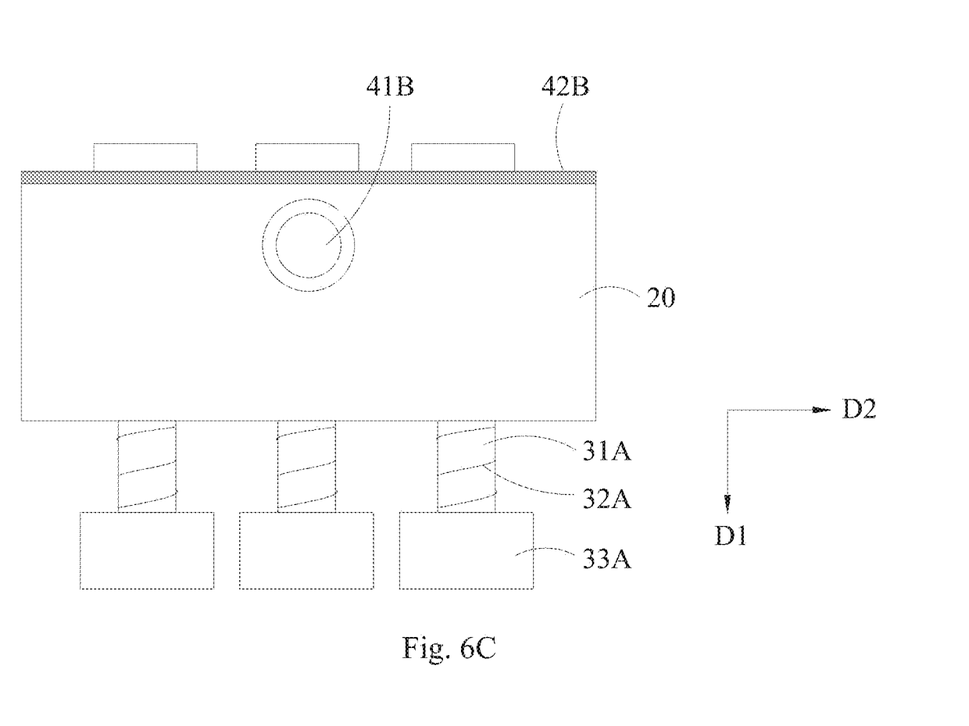
FIG. 6C is a schematic diagram of a sensing module and a first assist element in a second condition of a second embodiment according to the present disclosure.

FIG. 6B and FIG. 6C are a schematic diagram of a sensing module and a first assist element in a first condition of a second embodiment according to the present disclosure, and a schematic diagram of a sensing module and a first assist element in a second condition of a second embodiment according to the present disclosure. As shown in FIG. 6B, the bearing 20 moves on the track 111 to be above a wrist of a patient (as shown in FIG. 1). The second assist element 50 fixes the bearing 20 to a position in the second direction D2. Each of the sensing units 33A contacts the pulse diagnosis positions cun, guan, and chi of the wrist of the patient. A distance separating each of the sensing units 33A and the bearing 20 changes from the first heights h1 (as shown in FIG. 3A) to second heights h2. According to different cun, guan, and chi of a wrist, the second heights h2 can thereby be different. A tester presses the button 41B such that the plurality of electromagnets 42B conducts electricity and produces a magnetic field, the plurality of electromagnets 42B are attracted in pairs according to the magnetic field, and the plurality of electromagnets 42B further fixes each of the driving elements 31A to a position in the first direction D1, such that each of the driving elements 31A stops moving. Namely, a position of each of the sensing units 33A is fixed, such that a method using the button 41B to fix the driving elements 31A is convenient for the tester to operate. As shown in FIG. 6C, when measurement of each of the sensing units 33A ends, the tester again presses the button so as to end electrical conduction to the plurality of electromagnets 42B, thereby releasing the fixing of the assist element on each of the driving elements 31A.

In summary of the above, the pulse diagnosis of the present disclosure adjusts the positions of the sensing units to match pulse diagnosis positions cun, guan, and chi of the patient through configuration of the driving elements and the flexible elements, thereby accurately measuring a pulse of the patient.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A pulse diagnosis apparatus, comprising:
a base having a motion module, wherein the motion module is arranged on the base and movable back and forth along a first direction;
a bearing arranged on the motion module, wherein the bearing comprises a first face and a second face opposite each other along the first direction;
a plurality of sensing modules, each of the sensing modules comprising a driving element, a flexible element, and a sensing unit, wherein each of the driving element passes through the bearing and is movable in the first direction, each of the driving elements comprises a first terminal and a second terminal, each of the first terminals is proximal to the second face, each of the second terminals is proximal to the first face, each of the flexible elements sleeves one of the driving elements, two terminals of each of the flexible elements respectively abut one of the second terminals and the bearing, and each of the sensing units is arranged at a terminal face of one of the second terminals; and
a first assist element arranged at a side of the bearing, for fixing each of the driving elements to a position in the first direction, wherein the first assist element comprises a button and a plurality of electromagnets, the button is arranged at the side of the bearing and is eclectically connected to the plurality of electromagnets, the plurality of electromagnets are arranged on the second face and surround the first terminals of the plurality of driving elements, and the button is triggerable to allow the plurality of electromagnets to conduct electricity such that a magnetic field is produced, the plurality of electromagnets are attracted to each other according to the magnetic field, such that each of the driving elements is fixed to a position in the first direction.

2. The pulse diagnosis apparatus according to claim 1, further comprising a plurality of positioning elements arranged on an inner side of the bearing.

3. The pulse diagnosis apparatus according to claim 2, wherein one of the positioning elements is proximal to one of the sensing modules.

4. The pulse diagnosis apparatus according to claim 1, wherein the first assist element comprises an operation lever and a lock element, the operation lever is arranged at an exterior side of the bearing and is connected to the lock element, the lock element corresponds to the plurality of driving elements and is arranged in the bearing, and the operation lever is configured to drive the lock element to fix each of the driving elements to a posit on in the first direction.

5. The pulse diagnosis apparatus according to claim 1, further comprising a second assist element, the second assist element is arranged at a side of the bearing for fixing the bearing to a position in a second direction, and the second direction is perpendicular to the first direction.

6. The pulse diagnosis apparatus according to claim 5, wherein the motion module comprises a track, and the bearing is arranged on the track and is movable on the track along the second direction.

7. The pulse diagnosis apparatus according to claim 1, further comprising an electronic device, wherein each of the sensing units is configured to sense a to-be-sensed portion and emit a sensing signal, the electronic device is electrically connected to each of the sensing units, and the electronic device is configured to integrate the sensing signals into a pulse pressure and display the pulse pressure.

* * * * *